(12) United States Patent
Kjølseth et al.

(10) Patent No.: US 9,340,420 B2
(45) Date of Patent: May 17, 2016

(54) PROTON CONDUCTING MEMBRANE

(75) Inventors: Christian Kjølseth, Oslo (NO); Per Christian Vestre, Jar (NO)

(73) Assignee: Protia AS, Oslo (NO)

( * ) Notice: Subject to any disclaimer, the term of this patent is extended or adjusted under 35 U.S.C. 154(b) by 0 days.

(21) Appl. No.: 13/578,361

(22) PCT Filed: Feb. 10, 2011

(86) PCT No.: PCT/EP2011/051970
§ 371 (c)(1),
(2), (4) Date: Aug. 10, 2012

(87) PCT Pub. No.: WO2011/098525
PCT Pub. Date: Aug. 18, 2011

(65) Prior Publication Data
US 2012/0310027 A1    Dec. 6, 2012

Related U.S. Application Data

(60) Provisional application No. 61/303,854, filed on Feb. 12, 2010.

(51) Int. Cl.
| | | |
|---|---|---|
| *B01D 53/22* | (2006.01) |
| *B01D 71/02* | (2006.01) |
| *B01J 19/00* | (2006.01) |
| *B05D 3/02* | (2006.01) |
| *C07C 5/32* | (2006.01) |
| *C01B 3/26* | (2006.01) |
| *C07C 2/76* | (2006.01) |
| *C07C 5/333* | (2006.01) |
| *H01M 4/90* | (2006.01) |

(52) U.S. Cl.
CPC ... *C01B 3/26* (2013.01); *C07C 2/76* (2013.01); *C07C 5/322* (2013.01); *C07C 5/333* (2013.01); *H01M 4/9033* (2013.01); *C01B 2203/0405* (2013.01); *C01B 2203/107* (2013.01); *C01B 2203/1047* (2013.01); *C01B 2203/1058* (2013.01); *C01B 2203/1064* (2013.01); *C07C 2521/04* (2013.01); *C07C 2523/22* (2013.01); *C07C 2523/26* (2013.01); *C07C 2523/28* (2013.01); *C07C 2523/42* (2013.01); *C07C 2523/44* (2013.01); *C07C 2523/50* (2013.01); *C07C 2523/745* (2013.01); *C07C 2523/755* (2013.01); *C07C 2529/24* (2013.01); *C07C 2529/48* (2013.01); *C07C 2529/70* (2013.01);
(Continued)

(58) Field of Classification Search
None
See application file for complete search history.

(56) References Cited

U.S. PATENT DOCUMENTS

| | | | |
|---|---|---|---|
| 2003/0144565 A1 | 7/2003 | Allison et al. | |
| 2004/0050713 A1 * | 3/2004 | Chuang et al. | 205/413 |

(Continued)

FOREIGN PATENT DOCUMENTS

| | | |
|---|---|---|
| EP | 2103586 A1 | 9/2009 |
| RU | 2381207 | 2/2010 |

OTHER PUBLICATIONS

Haugsrud, Defects and transport properties in Ln6WO12 (Ln=La, Nd, Gd, Er), 2007, Solid State Ionics, vol. 178, pp. 555-560.*

(Continued)

*Primary Examiner* — Colin W Slifka
(74) *Attorney, Agent, or Firm* — Meunier Carlin & Curfman LLC

(57) ABSTRACT

A reactor comprising a first zone comprising a dehydrogenation catalyst and a second zone separated from said first zone by a proton conducting membrane comprising a mixed metal oxide of formula (I) $Ln_aW_bO_{12-y}$ wherein Ln is Y or an element numbered 57 to 71; the molar ratio of a:b is 4.8 to 6, preferably 5.3 to 6; and y is a number such that formula (I) is uncharged, e.g. y is $0 \leq y \leq 1.8$.

18 Claims, 4 Drawing Sheets

Planar design illustrating the support (layer 1), the membrane (layer 2) and the catalyst (layer 3).

(52) U.S. Cl.
CPC ............ *C07C 2529/85* (2013.01); *Y02E 60/50* (2013.01); *Y10T 428/24997* (2015.04)

(56) References Cited

U.S. PATENT DOCUMENTS

2005/0252853 A1    11/2005   Berland et al.
2006/0013759 A1*   1/2006    Jiang et al. .................. 423/648.1
2010/0233056 A1*   9/2010    Luo et al. ....................... 423/263

OTHER PUBLICATIONS

Escolastico, S., et al., Chemistry of Materials, 21(14):3079-3089 (2009).
Haugsrud, R., et al., Solid State Ionics, 178:555-560 (2007).
Haugsrud, R., et al., Journal of Physics and Chemistry of Solids, 69:1758-1765 (2008).
Magraso, A., et al., Dalton Transactions, pp. 10273-10283 (2009).
Shimura, T., et al., Solid State Ionics, 143:117-123 (2001).

* cited by examiner

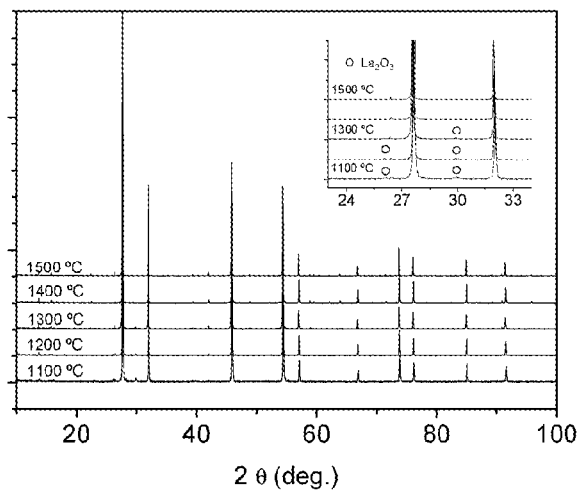
Figure 1:
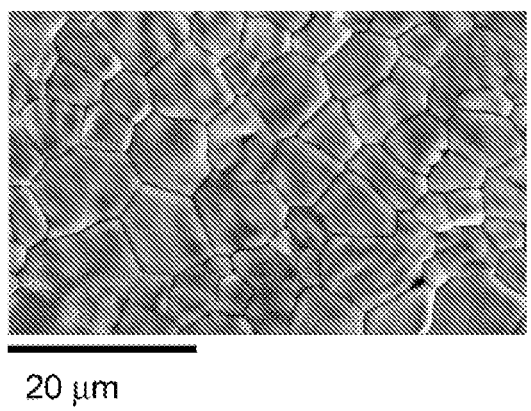
Figure 2:
Figure 3: Planar design illustrating the support (layer 1), the membrane (layer 2) and the catalyst (layer 3).

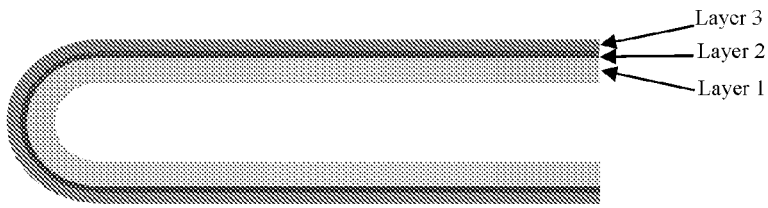
Figure 4: Tubular design illustrating the support (layer 1), the membrane (layer 2) and the catalyst (layer 3).
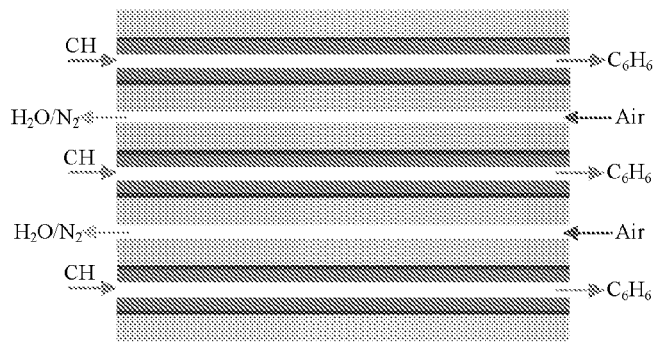
Figure 5: A simple planar reactor design alternative with a counter flow arrangement. The end product is benzene, $C_6H_6$.
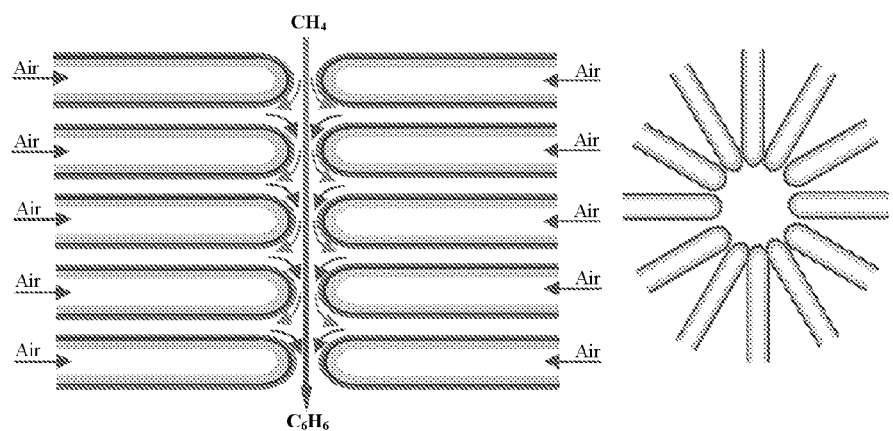
Figure 6: Right: a simple illustration of a tubular reactor design, where the end product is benzene, $C_6H_6$. Left: the tubular reactor seen from above.

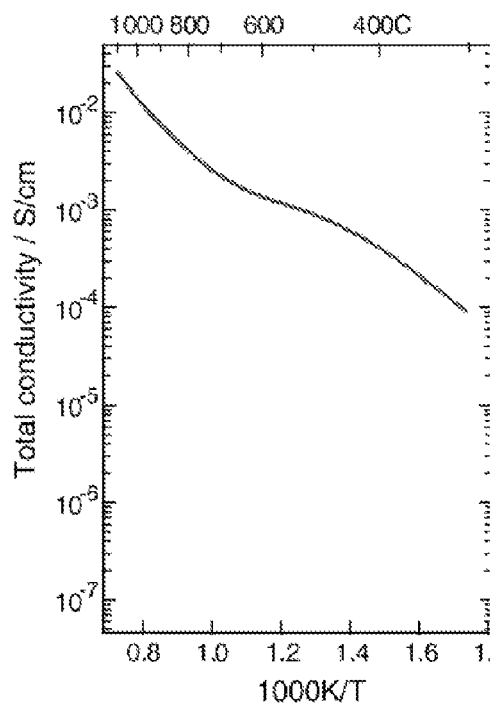
Figure 7: Total conductivity vs inverse absolute temperature of nominally undoped $La_6WO_{12}$ in wet $H_2$ ($pH_2O$ = 0.025 atm)

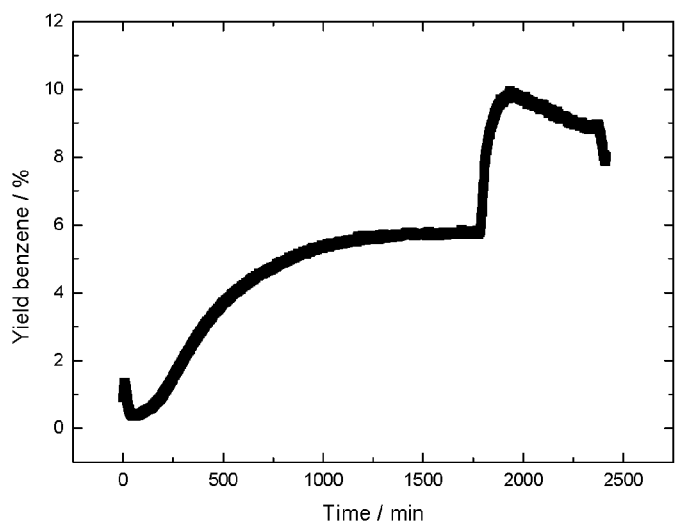
Figure 8. Theoretical Time evolution of yield benzene from methane over Mo-HZSM-5 catalyst at 600 °C in catalytic reactor mode and membrane catalytic reactor mode from approximately 1750 min.

PROTON CONDUCTING MEMBRANE

This invention relates to a proton conducting membrane which can be used to enable dehydrogenation reactions, in particular, alkane to alkene transformation. More specifically, the invention relates to the use of a mixed metal oxide in the manufacture of a proton conducting membrane.

BACKGROUND

With depletion of global liquid petroleum reserves, natural gas, containing primarily methane, is expected to be one of the main resources for the production of liquid fuels. However, direct dehydrogenation of light alkanes like methane and ethane to more valuable petrochemical products, e.g. olefins, aromatics (hereafter denoted olefin/aromatics) remains challenging.

For ethane to olefin/aromatics production, commercial processes include steam cracking and catalytic dehydrogenation, and recently there has also been renewed interest in oxidative dehydrogenation.

Oxidative dehydrogenation offers direct conversion from alkanes into valuable chemicals. By adding oxygen discretely through either porous or dense oxygen permeable membranes, the alkane to oxygen ratio can be kept high promoting high $C_{2+}$ selectivity.

A somewhat less investigated route for alkane conversion to fuels is through non-oxidative reactions. Here, using methane as an example, a coupling/dimerization/pyrolysis (hereafter denoted coupling) reaction takes place on the methane side of a reactor with hydrogen permeating through a membrane in the form of protons onto the oxygen side, where it reacts with oxygen to form water.

Oxygen is not present in the methane coupling compartment, avoiding the oxidation of methane. A high $C_{2+}$ selectivity may thus be expected. This is a highly efficient way to make olefins/aromatics from alkanes compared to existing technologies.

It has been shown theoretically that removal of hydrogen during coupling promotes homogeneous reaction pathways and shifts the equilibrium towards the product side. A hydrogen selective membrane in the process stream should therefore increase the yield considerably. The removal of hydrogen can be achieved using hydrogen permeable membranes.

Several such membranes exist. Catalytic dehydrogenation of ethane in a hydrogen membrane reactor has been investigated using a microporous silica membrane and a 5.0 wt. % $Cr_2O_3/\gamma$—$Al_2O_3$ catalyst prepared by incipient wetness impregnation of a $\gamma$—$Al_2O_3$ support.

A Pd—Ag composite membrane supported on porous stainless steel prepared by electroless plating has been used in a catalytic membrane reactor utilizing a Ru—Mo/HZSM-5 catalyst.

Using the ceramic mixed proton-electron conductor $SrCe_{0.95}Yb_{0.05}O_{3-\delta}$ a membrane configuration and also a co-generative fuel cell has been developed towards methane coupling.

There are problems with all these solutions however. Microporous membranes suffer from being fragile and difficult to make. Their hydrogen selectivity is also poor.

Pd—Ag membranes are inherently very expensive and whilst complex membranes have been formed in an attempt to minimise expensive metal content, there remains a desire to have a much simpler membrane. The catalytic activity of these metals towards formation of coke is also a considerable problem if these materials are used in a catalytic membrane reactor.

Ceramic oxides offer a more attractive option therefore. However, even initiatives using ceramic proton conducting materials have serious limitations. The prior art ceramic oxides are based on Ba- and Sr-based perovskites. These compounds are basic and react with $CO_2$ and $H_2S/SO_2/SO_3$ at moderate temperature and $H_2O$ at low temperatures to form alkaline earth carbonates, sulphates and hydroxides, respectively. Consequently, a decrease in conductivity is observed.

These reactions are prohibitive if using any carbon-containing feed gas as the impurities in the gas react with the membrane. Moreover, the reaction with carbon dioxide precludes the use of air in a reactor meaning expensive inert gases have to be used. Moreover, the electrical and mechanical properties of these materials become poor due to the formation of carbonates and hydroxides.

There remains therefore a need to develop new membrane materials which avoid the problems of the prior art. The inventors have found that a membrane based on mixed metal tungstates offers an ideal solution to this problem. These materials are stable in the presence of carbon dioxide and acidic gases in general making them usable in the presence of air. This also means the membranes can be used in the presence of hydrocarbon feed gases.

Moreover, the inventors have realised that the tungstates form an ideal membrane as they offer just the right hydrogen selectivity for an alkane to alkene, or more generally to olefin/aromatic dehydrogenation process. If too much hydrogen is allowed through the membrane, that simply encourages the equilibrium of the reaction to move too far to the right and hence to the formation of carbon itself. There are in fact membranes with better hydrogen selectivity but the use of such membranes in this reaction is actually detrimental. The membranes of the present invention ensure that the amount of hydrogen which passes through the membrane is sufficient to allow alkene (olefin/aromatic) formation but not coke formation.

It is an important feature of the invention that the inventors have appreciated that the proton membrane of the invention should not be too good a proton conductor as that is actually a problem rather than an advantage as it encourages coke formation and not alkene formation.

The mixed metal oxide used in the membrane is not itself new. In Solid State Ionics, 143 (2001), 117-123, the authors investigate the proton conducting properties of lanthanum tungstates. The present inventors have realised that these proton conducting materials, as opposed to the numerous other proton conducting materials known, offer the most attractive properties for use in dehydrogenation reactions, in particular of alkanes to alkenes (olefins/aromatics).

Thus, viewed from one aspect the invention provides a reactor comprising a first zone comprising a dehydrogenation catalyst and a second zone separated from said first zone by a proton conducting membrane comprising a mixed metal oxide of formula (I)

$$Ln_aW_bO_{12-y} \qquad (I)$$

wherein Ln is Y or an element numbered 57 to 71;
the molar ratio of a:b is 4.8 to 6, preferably 5.3 to 6; and
y is a number such that formula (I) is uncharged, e.g. y is $0 \leq y \leq 1.8$.

Viewed from another aspect the invention provides a reactor comprising a first zone comprising a dehydrogenation catalyst and a second zone separated from said first zone by a proton conducting membrane comprising at least one mixed metal oxide of formula (II)

$$Ln_aW_{b-c}Mo_cO_{12-y} \qquad (II)$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is 0≤y≤1.8.

Viewed from another aspect the invention provides a process for the dehydrogenation of substance, e.g. an alkane, comprising introducing said substance into the first zone of a reactor as hereinbefore defined to thereby dehydrogenate said sub stance;

allowing hydrogen formed during said dehydrogenation to pass through said proton conducting membrane into said second zone;

introducing a purge gas into said second zone, preferably to react with the hydrogen; or applying reduced pressure in said second zone to thus remove hydrogen from said second zone.

Viewed from another aspect the invention provides a proton conducting membrane comprising a dehydrogenation catalyst and a mixed metal oxide of formula (I)

$$Ln_aW_bO_{12-y} \tag{I}$$

wherein Ln is Y or an element numbered 57 to 71;
the molar ratio of a:b is 4.8 to 6, preferably 5.3 to 6; and
y is a number such that formula (I) is uncharged, e.g. y is 0≤y≤1.8.

Viewed from another aspect the invention provides proton conducting membrane comprising a dehydrogenation catalyst and a mixed metal oxide of formula (II)

$$Ln_aW_{b-c}Mo_cO_{12-y} \tag{II}$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is 0≤y≤1.8.

Viewed from another aspect the invention provides the use of a proton conducting membrane as hereinbefore defined in a dehydrogenation process.

DETAILED DESCRIPTION OF THE INVENTION

Mixed Metal Oxide

It is preferred if the proton conducting membrane of the invention comprises a single phase mixed metal oxide.

It is also preferred if the mixed metal oxide has electron conductivity as well as proton conductivity.

It is also preferred if the mixed metal oxide has a fluorite type crystal structure.

The metal oxide is preferably a rare-earth tungstate having general formula (I)

$$Ln_aW_bO_{12-y} \tag{I}$$

wherein Ln is Y or an element numbered 57 to 71;
the molar ratio of a:b is 4.8 to 6, preferably 5.3 to 6; and
y is a number such that formula (I) is uncharged, e.g. y is 0≤y≤1.8.

In a preferred embodiment, the mixed metal oxide is of formula (III):

$$Ln_xWO_{12-y'} \tag{III}$$

wherein Ln is Y or an element numbered 57 to 71 of the periodic table;
x is 4.8 to 6, preferably 5.5≤x≤6; and
y' is 0≤y'≤1.8.

It is preferred if the ratio of Ln to W (i.e. the ratio of a to b) is in the range 5.3 to 6, preferably 5.5 to 5.8, especially 5.6 to 5.7. In this embodiment therefore one or both of the Ln or W sites in the mixed metal oxide may by stiochiometric or non stiochiometric. The stoichiometric oxide is $Ln_6WO_{12}$.

The value of x in formula (III) is preferably 5.3 to 6, preferably 5.5 to 5.8, especially 5.6 to 5.7. This embodiment applies when the W site in the mixed metal oxide is stoichiometric.

It will be appreciated that the value of y (and y') is intrinsically linked to the amounts of Ln and W present. Depending on the oxidation state of the Ln ion and the amount of W present, the value of y required to balance the formula can be found. This value ensures therefore that the mixed metal oxide is uncharged.

It is within the scope of the invention for the y group to be a negative number, symbolising therefore a compound with more than 1 equivalent of W. Such a composition is discussed in FIG. 7.

Preferably the ratio of Ln/W and subscript "y" are related so that the compound of formula (I) is uncharged for a $Ln^{3+}$ ion, $W^{6+}$ ion and $O^{2-}$ ion.

For a completely stoichiometric compound in which Ln is in the 3+ oxidation state, a is 6, b is 1 and y is zero.

The subscript y' is preferably in the range 0 to 0.75, preferably 0.1 to 0.75, especially 0.25 to 0.75, most especially 0.5 to 0.75. It will be appreciated therefore that the values of x and y' in formula (III) correspond to give an uncharged mixed metal oxide, thus, if y' is 0.75 then x is 5.5 and so on.

Ln is preferably Y or an element numbered 57 to 71. Ln is preferably La, Y, Tb, Nd, Gd, Er and Eu. Ideally, Ln is La, Nd, Gd, Er and Eu. The metal ion Ln is preferably La.

Ln is preferably in the 3+ oxidation state.

The W ion is in the 6+ oxidation state.

In an alternative embodiment, the mixed metal oxide can be one in which W can be partially substituted with Mo. Such an oxide is therefore of formula (II)

$$Ln_aW_{b-c}Mo_cO_{12-y} \tag{II}$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is 0≤y≤1.8.

Mo can therefore substitute for up to half the amount of W and hence c can be up to 0.5×b. The ratio of Ln to W+Mo must be 4.8 to 6, i.e. the ratio a to (b−c)+c must be 4.8 to 6. It will be appreciated therefore that this reduces to a:b.

Preferably, c is 0.3 to 0.5b, i.e. 30 to 50 wt % of W is exchanged for Mo. The presence of the Mo will increase the electronic conductivity of the material. The preferred embodiments discussed above in relation to formula (I) also apply to formula (II). Thus the preferred Ln metals, a and b values, y values and ratios are as above. The Mo ion is preferably in the 6+ oxidation state.

In a preferred embodiment, the mixed metal oxide is of formula (IV):

$$Ln_xW_{1-c}Mo_cO_{12-y'} \tag{IV}$$

wherein Ln is Y or an element numbered 57 to 71 of the periodic table;
x is 4.8 to 6, preferably 5.5≤x≤6; c is 0 to 0.5; and
y' is 0≤y'≤1.8.

The preferred values for y' are as above. The subscript c is preferably 0.3 to 0.5.

Nevertheless, the mixed metal oxide of the invention should preferably not be doped on the Ln site. Ideally the mixed metal oxide should not be doped on the W site (i.e. is Mo free). Most preferably, the mixed metal oxide is not doped on either the Ln or W site.

It is within the scope of the invention for a mixture of mixed metal oxides to be employed in the membrane of the invention, e.g. a mixture of mixed metal oxides of formula (II). The use of a mixture of mixed metal oxides may increase electronic conductivity and could result in a higher overall hydrogen permeation. In one embodiment, the mixed may involve a mixed metal oxide of formula (I) and an MO doped mixed metal oxide of formula (II). Alternatively, the mixture may involve at least two mixed metal oxides of formula (I).

The proton conductivity of the tungstates of the invention may be at least $1 \times 10^{-3}$ S/cm, preferably at least $1.5 \times 10^{-3}$ S/cm, especially at least $2 \times 10^{-3}$ S/cm. These mixed metal oxides are not new and have been prepared before. Their synthesis is described in inter alia, Solid State Ionics 143 (2001) 117-123. Thus, the mixed metal oxides can be prepared by solid state reaction using, for example lanthanum oxide and tungstic acid. Sintering at temperatures of 1500° C. or more allows formation of the oxide. As noted below, in some embodiments, the mixed metal oxide may be used also a support structure. This method is a favourable route to fabricate mixed metal oxide to be used as the support. It tends to produce porous materials.

More recently, the mixed metal oxide of the invention has been manufactured using freeze drying synthesis (Dalton Trans 2009, 10273-10283). The method utilises lanthanum oxide and $WO_3$ mixed in ammonium hydroxide to which EDTA was added. The solution is flash frozen, freeze dried and calcined to form mixed metal oxides. Here dense samples were obtained at a sintering temperature of 1400° C. This route for the manufacture of the tungstates of the invention is favoured in the application.

The mixed metal oxide of the invention has also been manufactured by a spray pyrolysis route. Stable aqueous solutions of the precursors (Ln and W) are standardized by thermogravimetry and mixed to provide the desired stoichiometry. The solutions are then spray pyrolysed. The atomized solution is decomposed in the hot zone of the furnace (850° C.) and a homogeneous metal oxide mixture is obtained. The as-prepared powders can then be calcined in air followed by ball milled in 100% ethanol for 24 hours, dried in a rotabavapor and sieved at 250 µm. Different calcination processing can be used, from 600-900° C., with preferred 700-800° C. This is a more favourable route for the manufacture of the tungstates of the invention when used as the membrane.

It is thus favourable to use spray pyrolysed powder for membrane formation and solid state reaction powder as a support material. This forms a further aspect of the invention.

In Chem Matter, 2009, 21, 3079-3089, a sol-gel complexation synthesis method is described for forming lanthanum tungstates. The art therefore enables the formation of the mixed metal oxides of the invention and any convenient technique can be used.

In order to introduce Mo ions into the mixed metal oxides of the invention, an amount of the Mo equivalent of the W compound typically employed in the synthesis can be used. Thus if the mixed metal oxide reaction involves compound WX then the skilled man can simply reduce the amount of WX and add an appropriate amount of MoX. For example $MoO_3$ can be employed instead of $WO_3$ and so on. The amount of Mo added is simply a reflection of the desired stoichiometry.

Manipulation of the stoichiometry is typically achieved by varying the amounts of starting material employed.

The solid phase material formed by these processes may need to be further manipulated to manufacture a membrane. Milling of these materials, where necessary, is achieved conventionally, e.g. using an agate mill and is typically carried out in alcohol, e.g. isopropanol. This is removed prior to a calcination step.

Calcination can take place at any useful temperature depending on the nature of the material, e.g. a temperature of from 700 to 1700° C., e.g. 800 to 1700° C. as is known in the art, e.g. 1000 to 1500° C. It is preferred if calcination is carried out until a single phase material is formed. This can be determined readily by X-ray diffraction analysis.

The powder can be pressed and sintered. Pressing and sintering can be carried out using known conditions. For example, pressing is typically carried out at ambient temperature in any standard press and sintering can occur at temperatures up to 1600° C., e.g. 800 to 1500° C., preferably 1000 to 1450° C., e.g. 1200° C. to 1400° C.

Powders formed by the processes above can be single phase and are typically micron to submicron in size and non agglomerated. Post calcination particles sizes can be 10 to 10000 nm, e.g. 10 to 1000 nm, preferably 100 to 800 nm, especially 200 to 600 nm in diameter. For membranes values are preferably 100 to 800 nm, especially 200 to 600 nm in diameter and for supports preferably 1000-8000, especially 1000-4000 nm in diameter.

Dehydrogenation Catalyst

The reactor of the invention must comprise a dehydrogenation catalyst. The specific catalyst depends on the specific reaction for which the membrane reactor is to be used but can be readily selected by the person skilled in the art. The dehydrogenation catalyst can form part of the actual membrane or the catalyst could simply be present in the first zone of the reactor. The skilled man can devise any suitable arrangement to ensure that the catalyst performs its desired function.

The dehydrogenation catalyst catalyses the dehydrogenation of the substance of interest. The dehydrogenation catalyst is preferably a porous catalyst but it should ideally have some electron and proton conductivity as these species may need to be transported through the catalyst on the membrane.

Any dehydrogenation catalyst can be used as long as it is able to operate under the conditions of the reaction described in detail below. It will also be preferred if the dehydrogenation catalyst can function in the presence of acids and air. Ideally, the catalyst used is one for dehydrogenation of alkanes.

Suitable catalysts include oxides of the first row of transition metals such as Ni, Fe, Pt, Ag, Pd and their alloys. These can be supported on alkali metal oxides. Suitable examples are $CrO_2$, $MoO_3$ and $V_2O_5$.

Some perovskite compounds may be suitable as catalysts such as those of formula $AB_{1-q}B'_qO_{3-z}$ where A=Ca, Sr or Ba; B=Ce, Tb, or Pr; B'=Ti, V, Cr, Mn, Fe, Co, Ni, or Cu or combinations thereof; and $0.02<q<0.5$.

Preferably, however, the catalyst is a zeolite. Preferred zeolites are those having the structure, CHA, MFI, TON and MTW. Specifically preferred structures are SAPO-34, SAPO-11, SAPO-44, ZSM-22 and ZSM-12, e.g. ZSM-2 (MTW like).

Highly preferred zeolites are ZSM-5 zeolites, especially HZSM-5 zeolites, where the metal may be Mo, W, Fe, V or Cr, listed starting with highest activity.

For methane dehydrogenation, the most preferred catalyst is a H-ZSM5 with an active metal with reported activity in the order Mo>W>Fe>V>Cr to form aromatic products For methane dehydrogenation, the most preferred catalyst is a SAPO-34 with an active metal to form olefin products.

For ethane dehydrogenation any of the above mentioned catalysts for methane is applicable, but preferred catalysts include alumina supported $CrO_2$, $MoO_3$ and $V_2O_5$.

The choice of metal depends on the design, the desired activity and the compatibility with the membrane reactor.

A catalyst can also be used in the second zone (reducing side) of the membrane, but this is not essential. This catalyst will aid conversion of hydrogen which passes through the membrane into water or other hydrogen sink.

Examples of such a catalyst are Ag, a lanthanum/cerium cobalt mixed metal oxide (e.g. $La_{1-q}Sr_qCoO_{3-z}$ where $0.2 \leq q \leq 0.5$, z to balance) or a mixed metal cobalt oxide (e.g. $ACo_{1-q1}M_{q1}O_3$ where A=Ca, Sr and Ba, and M=Fe, Co and Ni where $0 \leq q1 \leq 0.5$.

These catalysts, typically in the form of powders, can be obtained commercially.

In one embodiment the catalyst will be deposited on the membrane. This will be achieved by techniques such as dip coating or impregnation, where the catalyst is dispersed in a solution. The membrane is then heat treated so that the catalyst is adhered to the membrane surface. The deposition can also be achieved by growing the catalyst directly on the membrane by a crystal growth technique.

A second embodiment includes a reactor where the catalyst is freely lying on top of, or in front of the membrane. The catalyst can be in the form of powder with tailored particle size. The catalyst is not adhered to the membrane. In this embodiment the catalyst can therefore easily be exchanged if it needs to be regenerated.

Support

It may be necessary to use a membrane support to carry the mixed metal oxide and/or catalyst. In some embodiments, the membrane of the invention is self supporting however, it is within the scope of the invention to use a support. The support should be inert, porous and capable of withstanding the conditions within the membrane reactor.

The following are important properties for the support:
Porous
Chemically compatible with the membrane—does not react to form a secondary insulating phase;
Mechanically compatible with the membrane—thermal expansion coefficient should preferably match that of the membrane.

The following are preferred properties of the support:
Catalytically active towards the formation of water;
Proton and electron conducting—to increase the number of triple phase boundaries where the formation of water take place;
Graded porosity towards the membrane to ease the deposition of the dense membrane.

Typically the support will be an inert metal oxide such as an alkali metal oxide or silica or alumina. Such supports are well known in this field. It is also possible to use a porous tungstate of the invention as the support or a doped tungstate of the invention as the support. These would chemically and mechanically match the membrane. This could be achieved by preparation of different particle size starting powders for membrane and support, which have different sintering properties, yielding a both a dense and a porous layer. In general, the particle size in the support should be greater than the particle size in the membrane, e.g. at least 200 nm higher.

As noted above, it is preferred if a spray pyrolysis method is used to form the membrane mixed metal oxide and solid state chemistry is used to form the support mixed metal oxide.

Thus, viewed from another aspect the invention provides a supported proton conducting membrane comprising a porous support and a non porous proton conducting membrane;

wherein said non porous proton conducting membrane comprises a mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is $0 \leq y \leq 1.8$; and
wherein said support comprises a porous mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is $0 \leq y \leq 1.8$.

This difference in porosity can be achieved by using different manufacturing techniques to form each component. Thus, spray pyrolysis can be used to form the dense, non porous membrane and solid state chemistry can be used to form the porous support.

Alternatively, the invention provides a supported proton conducting membrane comprising a support and a proton conducting membrane;

wherein said proton conducting membrane comprises a mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is $0 \leq y \leq 1.8$ having a particle size of 100 to 800 nm in diameter;
and wherein said support comprises a mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6, preferably 5.3 to 6; c is 0 to (0.5×b); and
y is a number such that formula (II) is uncharged, e.g. y is $0 \leq y \leq 1.8$ having a particle size of 1000-8000 nm in diameter.

Supports may be 2-300 µm to 1 mm or more in thickness.

The design of the support material depends on the design of the whole reactor. Typically the membrane, and hence any support, will be planar or tubular. The term tubular is used herein to designate a membrane is in the shape of a "test tube", i.e. a cylinder with hemispherical end portion but open at the other end.

In a tubular embodiment porous support tubes can be extruded. Both thermoplastic and water based extrusion processes can be used. The support is then heat treated to yield the desired mechanical strength. In a planar embodiment the support material can be tape cast, also followed by heat treatment to yield the desired mechanical strength. In a tape casting process, a slurry of the oxide is typically spread evenly onto a flat horizontal surface by means of a doctor blade. After drying, the thin, film formed can be removed, cut to the desired shape and fired.

To manufacture a support structure either as a planar support or as a tube, an ink of the desired support material can be produced either using water as a solvent or an organic solvent, optionally as well as stabilizing agents. To have controlled porosity, a pore filler material is often used, e.g. carbon black. The ink can then be tape cast or extruded. The support is subsequently fired to a desired firing temperature, such as 600 to 1500° C. to yield mechanical robust supports with a desired porosity.

In a complex design embodiment, the porous support tubes can be prepared by gel casting. A mould is prepared of the desired structure. A solution of the desired material is then prepared and poured into the mould. After the solution is gelified the mould is removed. The support is subsequently fired to a desired firing temperature, such as 600 to 1500° C. to burn out the organic residue and to yield mechanically robust supports with a desired porsity.

Membrane

In the simplest embodiment, the membrane is self supported. An oxide made as described above can simply be employed as a membrane. It is preferred, however, if the membrane of the invention is multilayered and is formed from a layer of the mixed metal oxide, a layer of the dehydrogenation catalyst and optionally a support layer. In use, it will be clear that the membrane must be oriented such that the dehydrogenation catalyst layer is nearer the first zone than the mixed metal oxide layer.

The proton conducting membrane will typically be formed using a layer of mixed metal oxide which may have a thickness of 1 to 50 micrometers, such as 5 to 20 micrometers. Altering the thickness of the proton conducting layer in the membrane can be used to adjust the selectivity of the reactor to protons.

The amount of catalyst in the membrane, i.e. the thickness of the catalyst layer may vary between 50 μm to 1 mm, e.g. depending on the targeted temperature, pressure and yield.

Alternatively, the membrane can be formed simply from the mixed metal oxide and optional support with the dehydrogenation catalyst forming, for example, a matrix within the first zone which the substance passes through.

Several thin film techniques can be used to deposit tungstate thin films. These include:
Screen printing;
Chemical vapour deposition techniques (CVD);
Spray deposition methods—e.g. ultrasonic spray deposition (USD);
Electrophoretic deposition;
Spin and dip coating;
Slurry coating; and
Impregnation.

Screen printing, spray deposition and spin/dip coating are preferred techniques. Screen printing is easy to upscale and can readily achieve thicknesses down to 10 μm.

The membrane will preferably be formed as a planar membrane or tubular membrane.

In a planar embodiment the membrane is preferably deposited on a porous support using a screen printing technique.

There are various options for membrane formation. The mixed metal oxide can be pre-formed and then used to form a membrane or precursors to the mixed metal oxide can be used to form a membrane with the final proton conducting membrane being formed upon calcination.

Thus, a homogeneous ink of the tungstate, preferably with particle size below 1 μm, preferably below 100 nm, most preferably below 10 nm can be fabricated using suitable organic chemicals. A mixed metal oxide powder such as $(Ln_6WO_{12})$, made by the methods described above, can be formed into a stable suspension. One way of achieving that is to disperse the mixed metal oxide in a binder with dispersing agents. Binders include the mixture of terpineol/ethyl-cellulose and dispersing agents are oleic acid and solsperse 3000. It is important that the dispersing agent burns off at relatively low temperatures to avoid carbon residues in the sintered product. This will give a stable suspension of the mixed metal oxide powder.

The support can then be dipped, using dip-coating technique, or the suspension is sprayed on the support using spray-coating technique, or the suspension is screen printed on the support, etc. The support-membrane assembly is then heat treated (150-400° C.) to ensure membrane to support binding.

In an alternative process, a mixed metal oxide precursor solution is used. The Ln and W ions (and optionally Mo ions) can be provided in the form of an organometallic, e.g. octylates of the Ln and W ions (and optionally Mo ions). These can form a stable ink with a suitable organic solvent. Organic solvents of use include alcohols such as isopropanol and amines such as diethanolamine or mixtures thereof.

The amounts of Ln and W ions (and Mo) present in the ink should be carefully measured to ensure that upon calcination a mixed metal oxide of formula (I)/(II) is formed. The amounts should obviously reflect the desired stoichiometry in the final oxide.

The ink is then printed on the porous support using a screen printer. The thickness of the membrane film is adjusted by varying the screen masks or the number of prints. Between each print the membrane-support assembly is dried to evaporate the volatile organic solvents. The membrane-support assembly is then fired in an oxygen containing gas (typically air), to the desired sintering temperature, which can be tailored to the particle size. This causes formation of the desired mixed metal oxide membrane. Calcination temperatures are those discussed above in connection with oxide manufacture.

The use of an organometallic compound of each cation to form a stable solution from which a membrane can be made is new and forms a still yet further aspect of the invention.

Thus viewed from another aspect the invention provides a process for the formation of a proton conducting membrane comprising a rare-earth tungstate having general formula (I)

$$Ln_aW_bO_{12-y} \tag{I}$$

as hereinbefore defined comprising forming a solution of an organometallic compound of Ln and an organometallic compound of W ions in an organic solvent,
forming a membrane on a support by coating said support with said solution, e.g. by dip coating or spray coating;
drying to remove said organic solvent; and
calcining to form said proton conducting membrane.

Viewed from another aspect the invention provides a process for the formation of a proton conducting membrane comprising a rare-earth tungstate having general formula (II)

$$Ln_aW_{b-c}Mo_cO_{12-y} \tag{II}$$

as hereinbefore defined comprising forming a solution of an organometallic compound of Ln and an organometallic compound of W ions and, if present, Mo ions in an organic solvent,
forming a membrane on a support by coating said support with said solution, e.g. by dip coating or spray coating;
drying to remove said organic solvent; and
calcining to form said proton conducting membrane.

Suitable organometallic compounds are alkylates, e.g. $C_{4-10}$ alkylates, especially octylates of the Ln or W/Mo ions.

In an alternative planar embodiment, the membrane can be deposited on the porous support using a spin coating technique. A homogeneous slurry of the tungstate (with particle size below 1 µm, preferably below 100 nm, most preferably below 10 nm) or precursor thereto can be made using suitable organic chemicals as described above. The slurry can then be deposited on the spinning support using spin coating apparatus. The thickness of the membrane film can be adjusted by the amount deposited and in addition the number of deposits. Between each deposit the membrane-support assembly can be dried to evaporate the volatile organic solvents. The membrane-support assembly is then fired to the desired sintering temperature, which can be tailored to the particle size.

For a tubular membrane, a preferred technique is deposition by spray coating. A stable suspension of the tungstate or precursors thereto is sprayed on the tubular support utilizing spray coating apparatus, to a suitable membrane film thickness. The coated tubes are then heat treated to suitable sintering temperature.

Dip coating is a further option here. A suspension (of tungstate or precursor) with desired wetting properties can be prepared and support tubes dipped in said suspension a selected number of times depending on the desired membrane film thickness with a drying stage in between each deposition. The membrane-support assembly can again be heat treated to suitable sintering temperature.

The skilled man is therefore able to prepare proton conducting membranes of the invention.

The principles of operation are not dependent on the structure of the reactor, and are therefore the same for a planar design and for a tubular design.

Membranes may need to be regenerated periodically. This can be achieved with an oxygen flush.

Reactor

The proton conducting membrane is used in a proton conducting membrane reactor. By reactor is meant a vessel in which the process of the invention can be carried out. The membrane can consist of three parts, the support, the mixed metal oxide and the catalyst. The reactor comprises the membrane, the catalyst (if that is not part of the membrane, and has a first zone and a second zone separated by the membrane formed from the mixed metal oxide.

In the first zone, the substance to be dehydrogenated is contacted with the dehydrogenation catalyst thus forming hydrogen and a dehydrogenated product. The hydrogen passes through the proton conducting membrane but as this membrane is selective, the dehydrogenated product remains within the first zone and can be collected from the outlet of the first zone.

In the second zone, hydrogen which has passed through the membrane is normally oxidised to water by reaction with oxygen or converted to some other hydrogen containing compound in an oxidation reaction. Alternatively, an inert purge gas could be used to remove hydrogen or a partial vacuum can be applied in the second zone to reduce hydrogen content. The idea here is to reduce the hydrogen content in the second zone to create a concentration gradient for the hydrogen between first and second zones. As hydrogen is dragged from first to second zone, the hydrogen concentration in the first zone decreases thus encouraging dehydrogenation in the first zone.

Preferably a purge gas passes through the second zone. As noted above, the mixed metal oxide is stable in the presence of air so air can be used as the purge gas. This is attractive as air is free unlike the inert gases conventionally used in the art.

In the presence of air, the hydrogen reacts with oxygen to form water which can be removed.

The process takes place at a temperature of 300 to 1200° C., preferably 400 to 900° C. It is preferred that the reactor is at this temperature when the substance to be dehydrogenated is added.

Note that the reaction of oxygen and hydrogen is exothermic so control over temperature may be required. However, the dehydrogenation reaction is endothermic. The process of the invention is typically carried out at a temperature of 300 to 1200° C., preferably 400 to 900° C. which means that the heat generated by the reaction of hydrogen and oxygen can also be used to maintain the temperature within the reactor as a whole.

It is also possible to use elevated pressure in the process of the invention.

As an alternative to an oxygen containing gas or inert purge gas, the hydrogen could be removed using a partial vacuum.

The reactor will have an inlet and an outlet in both zones to allow reactants in and products/wastes out of the reactor.

The first zone will therefore comprise an inlet for the substance to be dehydrogenated and an outlet for the dehydrogenated product. It will be appreciated that some unreacted substance may also be removed and a separation of product/reactant may be required. Unreacted substance can of course be feed back to the reactor.

In some embodiments, the second zone will also have an inlet for purge gas and an outlet for removing purge gas and hydrogen/purge gas reaction products. Alternatively, the second zone may just have an outlet for removing hydrogen using a vacuum.

The skilled man will be able to devise reactor set ups to carry out the process herein. FIGS. 5 and 6 exemplify options for reactor set up and the principles therein can be applied to the invention as a whole. It is preferred therefore if any purge gas flows counter current to the feed gas being dehydrogenated.

Substance

It is preferred if the compound for dehydrogenation is a hydrocarbon, especially a saturated hydrocarbon such as an alkane or cycloalkane. Especially preferably the alkane is a $C_{1-4}$ alkane, most especially methane (e.g. natural gas), ethane, propane or butane.

Methane is dehydrogenated according to the equation:

$$2CH_4 \rightarrow C_2H_6 + H_2 \rightarrow C_2H_4 + H_2 \rightarrow C_2H_2 + H_2 \rightarrow 2C(s) + H_2$$

Using a Mo HZSM-5 catalyst, the mechanism of the reaction seems to involve the conversion of $CH_4$ to $C_2H_4$ on e.g. molybdenum carbide or oxycarbide and further conversion of $C_2H_4$ to aromatic products over the acidic sites within the channels of the zeolite.

It will be appreciated that the dehydrogenation reaction needs to be stopped before the formation of coke. This is achieved using a combination of factors such as the ideal conductivity of the membrane, and a suitable catalyst. Temperature and pressure can also be used to adjust the equilibrium of the above reaction.

It will also be appreciated that any alkene formed may dimerise or trimerise under the conditions in the reactor to form, for example benzene.

The conversion of substance achieved in this invention is preferably at least 95 wt %, preferably at leas 97 wt %, e.g. 99 wt % or more. This means that almost all the substance (typically an alkane) fed to the reactor is converted to the dehydrogenated desired product (typically an alkene).

Moreover, it is preferred if the selectivity is preferably at least 95 wt %, preferably at leas 97 wt %, e.g. close to 100 wt %. This means that the formed dehydrogenated product is at least 95 wt % pure, i.e. there are almost no impurities present at all.

Further, compared to using complex metal membranes or unstable perovskites of the prior art, the mixed metal oxide material of this invention is stable even in chemically harsh conditions at high temperatures.

It is also envisaged that the membrane and reactor of the inventor could be used in the decomposition of hydrogen sulphide. The tungstates of the invention are stable in sulphur containing atmospheres, and are therefore ideal for use in $H_2S$ decomposition. Here, the catalyst used should be one that enables hydrogen sulphide decomposition such as thiospinels $AB_2S_4$ (where A is a 2+ group VIII ion and B is a 3+ group VIII ion e.g. $FeFe_2S_4$) or $WS_2$.

The invention will now be further described with reference to the following non limiting examples and Figures.

BRIEF DESCRIPTION OF THE FIGURES

FIG. 1 shows the evolution of the XRD patterns with temperature for sintering temperatures of 1100 to 1500° C. The nominal La/W ratio is 5.5. (Diffractogram taken from Magraso et al. Dalton Transaction, (2009), 10273-10283).

FIG. 2 shows a SEM micrograph of the surface of a disk of the tungstate of the invention with a grain size of ~10 μm sintered at 1500° C. The nominal La/W ratio is 5.6. (Micrograph taken from Magraso et al. Dalton Transaction, (2009), 10273-10283).

A catalyst-membrane-support structure is illustrated in FIG. 3. The first layer comprises the support. The second layer comprises the membrane. The third layer comprises the catalyst. This layer can be adhered to the membrane surface or freely lying on top.

A tubular catalyst-membrane-support structure/design is illustrated in FIG. 4. Two general designs are possible. One, see FIG. 4, with the catalyst layer on the surface (layer 3) of the tube, followed by the membrane (layer 2) and the support on the inside of the tube (layer 1), and one (not illustrated) with the catalyst layer on the inside of the tube. The arrangement shown in FIG. 4 with the catalyst layer on the surface of the tube is advantageous if the dehydrogenation reaction is slow. If the reduction reaction of $O_2$ and/or the water formation reaction and/or the diffusion of water/$O_2$ to the membrane are the slowest the arrangement with the catalyst layer inside the tube will be advantageous.

An embodiment for a planar reactor design is illustrated in FIG. 5. Modules of catalyst-membrane-support assemblies are stacked horizontally arranged so that the support faces a support of a second assembly, and the catalyst faces a catalyst of a third assembly and so on. This stacking form channels for the reactant gas and the purge gas respectively. Each assembly is sealed at the end with suitable sealing material, such as a glass which is non-catalytically active towards coke formation.

The embodiment shown has a counter-current gas flow. This configuration has a similar hydrogen pressure gradient ΔP in the two end segments. The first segment is located at the inlet of the reactant gas. The hydrogen concentration will be highest at this point, while the oxygen content in the purge gas will be the lowest. In the other end, of the air inlet, the hydrogen pressure will be at the lowest point, while the oxygen pressure will be at the highest. The pressure gradient in the two ends will be approximately equal, which is also true for the part between the two ends. This will ensure a homogeneous dehydrogenation along the membrane, which furthermore will stabilize the conversion towards carbon formation. In this way a constant thickness of the membrane can be used throughout the reactor.

A tubular reactor design is illustrated in FIG. 6. In this design tubes with the catalyst on the surface are stacked in a circular, horizontal matter, as seen in FIG. 6. The reactant is fed from the top of the reactor, and is lead downwards, where it distributes evenly and converts to unsaturated hydrocarbons. The inside of the tubes are fed with air, and the flow is adjusted so that the exhaust of nitrogen and water are readily transported out.

In this embodiment, if a tube is in the top layer, the concentration of hydrocarbon will be high and therefore also the conversion. Further down in the reactor, the concentration of hydrocarbon will decrease and therefore also the conversion. A consequence of this design might be an uneven degradation of the tubes, due to higher coke formation in the tubes with the highest conversion.

This can be solved either by adjusting the membrane thickness of the tube, so that the conversion becomes even throughout the reactor, or by regenerating the degenerated tubes.

Each tube is sealed by preferably a glass sealant which is non-catalytically active towards coke formation. The temperature at the sealant part of the tubes is lower than that inside the reactor and enables therefore the usage of lower temperature sealant materials.

FIG. 7 illustrates the proton conductivity of a nominally undoped stiochiometric $La_6WO_{12}$ mixed metal oxide dependent on temperature measured at a constant 10 kHz frequency. (Graph taken from Haugsrud et al. Solid State Ionics, (2007), 555-560).

FIG. 8 is a theoretical plot of benzene yield as a function of time. The plot can be divided up in four zones. Zone 1 shows that the catalyst needs some time to be activated. Approaching 1250 min the yield starts to stabilize at approximately 5% under a catalytic reactor mode. In zone 3 at ~1750 min the mode is switched to catalytic membrane mode and the yield increases dramatically.

EXAMPLE 1

Oxide powder was produced using a freeze-drying precursor route (Magraso et al. Dalton Transactions, (2009), 10273-10283). Stoichiometric quantities of $La_2O_3$ and $WO_3$ were dissolved in diluted nitric acid and ammonium hydroxide solution respectively. $WO_3$ dissolves in aqueous alkaline solution to form tungstate ions, $[WO_4]^{2-}$.

Ethylenediamineteraacetic acid was added to each of the solutions as complexing agent in a 1:1 molar ratio ligand:metal and the pH is adjusted to 7-8. After neutralization, both cation solutions were mixed without any visible precipitation. Droplets of this transparent solution were subsequently flash frozen in liquid nitrogen, and then freeze-dried for 3 days. In this way, an amorphous precursor was obtained, which was immediately fired at 300° C. for 15 min to prevent hydration. The powder was further calcined at 600° C. for 2-4 hours until a white powder was obtained, in order to ensure complete decomposition of the organics in the precursor. The powder was subsequently calcined at 1100-1500° C. for 2 h, and characterized by powder X-ray diffraction. The XRD pattern for a powder calcined at 1100-1500° C. is given in FIG. 1. The powder becomes single phase above 1400° C. as seen from the diffractogram.

The nominal La/W ratio is 5.5, i.e. the a:b ratio is 5.5.

EXAMPLE 2

A disk of 10 mm in diameter and 1 mm in thickness were prepared by pressing powder prepared following the protocols of example 1 with a nominal La/W ratio of 5.6, calcined at 1000° C. at 100 MPa. The resulting specimen was sintered in air at 1500° C.

FIG. 2 shows a SEM micrograph of the surface of the specimen with a grain size of ~10 μm.

EXAMPLE 3

An alumina support is coated with the tungstate of the invention by dip coating. The support is dipped into a solution of octylates of La and W in a solution using iso-propanol and diethanolamine with a drying stage in between each deposition. The membrane is then heat treated at a temperature of 800° C. so that the catalyst is adhered to the membrane surface.

EXAMPLE 4

An alumina support is coated with the tungstate of example 1 by dip coating. The support is dipped into a solution of octylates of La and W in a solution using iso-propanol and diethanolamine with a drying stage in between each deposition.

Thereafter, the porous support/mixed metal oxide structure is dipped in a solution of HZSM-5 (active metal Mo) with a drying stage in between each deposition.

The membrane is then heat treated at a temperature of 800° C. so that the catalyst is adhered to the membrane surface.

EXAMPLE 5

The membrane of example 4 is used in the dehydrogenation of methane using a reactor set up as described in FIG. 5 or 6.

EXAMPLE 6

A catalytic membrane reactor is prepared using a $La_{5.6}WO_{12-\delta}$ hydrogen permeable membrane tube and 3 wt % Mo impregnated HZSM-5 (as dehydrogenation catalyst). In the reactor 3 grams of the catalyst is freely lying in front (around) the membrane. The catalyst is not adhered to the membrane. It can therefore easily be exchanged if it needs to be regenerated.

Pre-treatment of the catalyst is done in the following manner: Gradual heating in air in temperature ramped mode up to 600° C. and then maintained at this temperature for 4 hours. Then the catalyst is treated in flowing air for 30 min at 600° C. and finally in 5% $H_2$/95% Ar mixture at 300° C. for 12 hours. After catalyst pre-treatment a 90% $CH_4$/10% Ar mixture is fed to the reactor at a relatively low mass-flow-controlled rate of ~300 mL(STP) $h^{-1}$ $g^{-1}$ methane hourly space velocity. The reaction is carried out under atmospheric pressure and at 600° C. Hydrogen permeation is ensured using a vacuum pump connected to the permeation zone providing a sufficient driving force for withdrawal of the hydrogen produced from the aromatization out of the reaction zone.

As illustrated in FIG. 8 the experiment is first carried out under catalytic reactor mode (without utilizing the hydrogen membrane). This mode gives a theoretical yield of benzene of ~5%, which is close to the thermodynamic barrier. At ~1750 min the mode is changed to catalytic membrane reactor mode by enabling the vacuum pump to remove hydrogen from the feed side to the permeate side of the membrane. As can be seen the theoretical yield increases to above 10% exceeding the thermodynamic barrier.

The invention claimed is:

1. A proton conducting membrane comprising a dehydrogenation catalyst and at least one mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6; c is 0 to (0.5×b); and
y is a number such that formula (II) is uncharged.

2. A membrane as claimed in claim 1 wherein Ln is La.

3. A membrane as claimed in claim 1 wherein said dehydrogenation catalyst is a zeolite catalyst.

4. A membrane as claimed in claim 3 wherein said zeolite has the structure CHA or MFI.

5. A membrane as claimed in claim 4 wherein said zeolite is a ZSM-5, with a metal selected from Mo, W, Fe, V or Cr.

6. A membrane as claimed in claim 1 wherein said molar ratio of a:b is 5.3 to 6.

7. A membrane as claimed in claim 1 wherein y is 0≤y≤1.8.

8. A membrane as claimed in claim 1 wherein the mixed metal oxide has a conductivity of at least $1 \times 10^{-3}$ S/cm.

9. A membrane comprising a dehydrogenation catalyst and at least one mixed metal oxide, wherein said mixed metal oxide is of formula (I)

$$Ln_aW_bO_{12-y} \quad (I)$$

wherein Ln is Y or an element numbered 57 to 71;
the molar ratio of a:b is 4.8 to 6; and
y is a number such that formula (I) is uncharged.

10. A membrane comprising a dehydrogenation catalyst and at least one mixed metal oxide, wherein the mixed metal oxide is of formula (III):

$$Ln_xWO_{12-y'} \quad (III)$$

wherein Ln is Y or an element numbered 57 to 71 of the periodic table;
x is 4.8 to 6; and
y' is 0≤y'≤1.8.

11. A supported proton conducting membrane comprising a porous support and a non porous proton conducting membrane thereon;
wherein said non porous proton conducting membrane comprises a mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6; c is 0 to (0.5×b); and
y is a number such that formula (II) is uncharged; and
wherein said support comprises a porous mixed metal oxide of formula (II)

$$Ln_aW_{b-c}Mo_cO_{12-y} \quad (II)$$

wherein Ln is Y or an element numbered 57 to 71;
the molar ratio of a:b is 4.8 to 6; c is 0 to (0.5×b); and
y is a number such that formula (II) is uncharged.

12. A supported proton conducting membrane as claimed in claim 11 wherein said non porous membrane is produced by spray pyrolysis and said porous support is produced by solid state reaction.

13. A supported proton conducting membrane as claimed in claim 11 wherein the particle size of the membrane is 100 to 800 nm in diameter and the particle size of the support is 1000-8000 nm in diameter.

14. A supported proton conducting membrane as claimed in claim 11 comprising a dehydrogenation catalyst on said proton conducting membrane so as to form the layered structure support-membrane-catalyst.

15. A reactor comprising a first zone comprising a dehydrogenation catalyst and a second zone separated from said first zone by a proton conducting membrane comprising a mixed metal oxide of formula (II)

$$Ln_aW_{b-c}Mo_cO_{12-y} \tag{II}$$

wherein Ln is Y or an element numbered 57 to 71;
the molar ratio of a:b is 4.8 to 6; c is 0 to (0.5×b); and
y is a number such that formula (II) is uncharged.

16. A process for the dehydrogenation of substance, comprising introducing said substance into the first zone of a reactor as claimed in claim 15 to thereby dehydrogenate said substance;
    allowing hydrogen formed during said dehydrogenation to pass through said proton conducting membrane into said second zone;
    introducing a purge gas into said second zone, preferably to react with the hydrogen; or
    applying reduced pressure in said second zone to thus remove hydrogen from said second zone.

17. A process for the formation of a proton conducting membrane comprising a rare-earth tungstate having general formula (II)

$$Ln_aW_{b-c}Mo_cO_{12-y} \tag{II}$$

wherein Ln is Y or an element numbered 57 to 71;
the molar ratio of a:b is 4.8 to 6; c is 0 to (0.5×b); and
y is a number such that formula (II) is uncharged, comprising forming a solution of an organometallic compound of Ln and an organometallic compound of W ions and if present Mo ions in an organic solvent,
forming a membrane on a support by coating said support with said solution;
drying to remove said organic solvent; and
calcining to form said proton conducting membrane.

18. A process as claimed in claim 17 wherein the step of forming a membrane on a support is by dip coating or spray coating.

* * * * *